(12) United States Patent
Ueda et al.

(10) Patent No.: US 7,021,031 B2
(45) Date of Patent: Apr. 4, 2006

(54) PROCESS FOR MAKING PRE-FORMED OBJECTS

(75) Inventors: Akihiro Ueda, Hyogo (JP); Gregory Michael McCabe, Cincinnati, OH (US); Kenneth Eugene Kyte III, Lebanon, OH (US); Koichiro Masuda, Osaka (JP); Masahiko Ishimoto, Kagawa (JP); Shin Seki, Kagawa (JP)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 11/099,709

(22) Filed: Apr. 6, 2005

(65) Prior Publication Data

US 2005/0172578 A1 Aug. 11, 2005

Related U.S. Application Data

(62) Division of application No. 10/316,639, filed on Dec. 11, 2001, now Pat. No. 6,899,840.

(60) Provisional application No. 60/339,287, filed on Dec. 11, 2001.

(51) Int. Cl.
*B65B 3/04* (2006.01)

(52) U.S. Cl. .............. 53/474; 53/435; 53/438; 53/440

(58) Field of Classification Search .......... 53/452, 53/453, 474, 435, 436, 438, 440; 264/171.13; 206/581, 484
See application file for complete search history.

(56) References Cited

U.S. PATENT DOCUMENTS

| | | | |
|---|---|---|---|
| 2,876,602 A * | 3/1959 | Ditlea | 53/452 |
| 3,896,061 A | 7/1975 | Tanzawa et al. | |
| 3,917,116 A * | 11/1975 | Mason | 206/484 |
| 4,372,098 A * | 2/1983 | Mason | 53/474 |
| 4,896,768 A * | 1/1990 | Anderson | 53/438 |
| 5,399,619 A | 3/1995 | Torradas et al. | |
| 5,419,958 A * | 5/1995 | Charbonneau | 428/315.5 |
| 5,426,008 A | 6/1995 | Hagiwara et al. | |
| 5,534,209 A | 7/1996 | Moryiya | |
| 5,682,726 A * | 11/1997 | Green et al. | 53/474 |
| 5,799,675 A * | 9/1998 | Gunderman et al. | 132/333 |
| 5,953,885 A * | 9/1999 | Berman et al. | 53/435 |
| 6,006,916 A * | 12/1999 | Matsos et al. | 53/452 |
| 6,074,725 A | 6/2000 | Kennedy | |
| 6,227,208 B1 * | 5/2001 | Imbert | 132/304 |
| 6,238,615 B1 | 5/2001 | Kobayashi et al. | |
| 6,354,308 B1 * | 3/2002 | Kuk | 206/581 |
| 6,375,871 B1 | 4/2002 | Bentsen et al. | |
| 6,660,203 B1 | 12/2003 | Fujimoto et al. | |
| 6,922,975 B1 * | 8/2005 | Shiraishi et al. | 53/436 |

FOREIGN PATENT DOCUMENTS

JP 6-321733 A 11/1994

(Continued)

*Primary Examiner*—Louis Huynh
(74) *Attorney, Agent, or Firm*—Juliet A. Jones (57) ABSTRACT

A continuous line process for making a packaged cosmetic device comprising a pre-formed sheet and a coating composition in a sealed package, wherein the pre-formed sheet is produced from a sol phase composition comprising a solvent and a gelling agent having a sol-gel transition point between about the melting point of the solvent and about the boiling point of the solvent by a process comprising heating the so phase composition, forming surfaces of the sol phase composition by pressing the sol phase composition between a plurality of liners, cooling the sol phase composition into a gel phase, cutting the gel phase composition to form the pre-formed sheet.

5 Claims, 7 Drawing Sheets

FOREIGN PATENT DOCUMENTS

| | | |
|---|---|---|
| JP | 9-095440 A | 4/1997 |
| JP | 10-014897 A | 1/1998 |
| JP | 10-057332 A | 3/1998 |
| JP | 10-095708 A | 4/1998 |
| JP | 10-121037 A | 5/1998 |
| JP | 10-258078 A | 9/1998 |
| JP | 11-130664 A | 5/1999 |
| JP | 11-269031 A | 10/1999 |
| JP | 11-335238 A | 12/1999 |
| JP | 2000-80016 A | 3/2000 |
| JP | 2000-119128 A | 4/2000 |
| JP | 2000-309522 A | 11/2000 |
| JP | 2001-518540 A | 10/2001 |
| WO | WO 01/78678 A1 | 10/2001 |

* cited by examiner

PROCESS FOR MAKING PRE-FORMED OBJECTS

CROSS-REFERENCE TO RELATED APPLICATIONS

This application is a Divisional application of application Ser. No. 10/316,639, filed Dec. 11, 2002 now U.S. Pat. No. 6,899,840, and claims the benefit of priority to U.S. Provisional Application No. 60/339,287, filed Dec. 11, 2001.

FIELD

The present invention relates to a continuous line process for making a pre-formed object, which is free of a supporting substrate, made of a composition comprising a solvent and a gelling agent having a sol-gel transition point between about the melting point of the solvent and about the boiling point of the solvent. The process is suitable for providing stable pre-formed objects in large scale manufacturing.

BACKGROUND

Pre-formed objects made of gelling agents, which are free of supporting substrates, provide unique benefits to various consumer products due to its formed, yet flexible physical characteristics. Pre-formed patch and mask devices are useful for cosmetic and dermatological treatment products such as for delivering skin care actives, percutaneously deliverable pharmaceuticals, and for promoting healing of burns or wounds. Edible pre-formed sheets and objects provide nutritional products and snacks having distinctive appearance and oral texture, and oral administrative pharmaceuticals.

Co-pending PCT application US/00/09694 relates to a pre-formed cosmetic device for delivering skin benefit agents to the skin, hair or nails, the cosmetic device comprising a solid gel sheet having opposed first and second surfaces, wherein the gel sheet comprises one or more gelling agents and topical acceptable hydrophilic solvent. In PCT application US/00/09694, injection molding is disclosed as a preferred embodiment for producing the gel sheet.

While injection molding is one effective method to provide pre-formed objects, particularly in small scale production, such method is not desirable for producing large quantities of pre-formed objects due to the complexity of instruments required to form the composition at controlled temperatures and speed. Further, in that forming of compositions containing gelling agents by injection molding require flash cooling of the composition, this may result in compositions that do not have a stable rheology. Unstable rheology of a pre-formed object having no supporting substrate may lead to unstableness of the form of the product, leaking of the product from the packaging, or ineffective delivery of actives via the product. All of such may significantly affect product performance and/or aesthetics.

Based on the foregoing, there is a need for a process for producing a stable pre-formed object which is free of a supporting substrate that can be applied to large scale manufacturing.

None of the existing art provides all of the advantages and benefits of the present invention.

SUMMARY

The present invention is directed to a continuous line process for making a pre-formed object having a plurality of surfaces comprising the steps of:
(1) providing a sol phase of the composition comprising a solvent and a gelling agent having a sol-gel transition point between about the melting point of the solvent and about the boiling point of the solvent;
(2) forming surfaces of the sol phase composition by passing through a surface forming system, the surface forming system pressing the sol phase composition between a plurality of liners;
(3) cooling the sol phase composition into a gel phase; and
(4) cutting the gel phase composition;
wherein the pre-formed object is free of a supporting substrate.

The process provides a process, particularly suitable for large scale manufacturing, for producing a stable pre-formed object which is free of a supporting substrate.

The present invention is further directed to a pre-formed object made by the process above.

The present invention is further directed to a use of the pre-formed object made by the process above as a cosmetic product, a pharmaceutical product, or a food product.

The present invention is further directed to a cosmetic device comprising the pre-formed object made by the process above and a coating composition.

The present invention is further directed to a cosmetic device comprising a pre-formed sheet having a first surface having a specified texture, and a coating composition of a specified viscosity.

These and other features, aspects, and advantages of the present invention will become better understood from a reading of the following description, and appended claims.

BRIEF DESCRIPTION OF THE FIGURES

While the specification concludes with claims particularly pointing out and distinctly claiming the invention, it is believed that the present invention will be better understood from the following description of preferred, nonlimiting embodiments and representations taken in conjunction with the accompanying drawings in which:

DEFINITIONS

All cited references are incorporated herein by reference in their entireties. Citation of any reference is not an admission regarding any determination as to its availability as prior art to the claimed invention.

Herein, "comprising" means that other steps and other ingredients which do not affect the end result can be added. This term encompasses the terms "consisting of" and "consisting essentially of".

All percentages, parts and ratios are based upon the total weight of the compositions of the present invention, unless otherwise specified. All such weights as they pertain to listed ingredients are based on the active level and, therefore, do not include carriers or by-products that may be included in commercially available materials. All measurements are conducted at 25° C. unless otherwise specified.

All ingredients such as actives and other ingredients useful herein may be categorized or described by their cosmetic and/or therapeutic benefit or their postulated mode of action. However, it is to be understood that the active and other ingredients useful herein can, in some instances, provide more than one cosmetic and/or therapeutic benefit or operate via more than one mode of action. Therefore, classifications herein are made for the sake of convenience and are not intended to limit an ingredient to the particularly stated application or applications listed.

The term "pre-formed" as used herein, means that the object is manufactured into a form having a predetermined shape and size, wherein the object may be removed from any associated packaging and placed or draped onto the target surface by the fingers without further preparative steps by the user. The term "pre-formed" also means that, when manufacturing is completed, the object substantially retains its shape at the desired normal storage temperature when lying on a flat surface. The composition may nevertheless flex or be deformed when applied to an uneven surface or if impressed.

The term "free of supporting substrate" as used herein, means the pre-formed object is uniform and unilamellar in composition, with no additional substrate or layer for aiding in the structure or integrity of the pre-formed object.

The term "sol phase composition" as used herein, means the composition for making the pre-formed object being in a sol phase state or an incomplete gel phase state during manufacturing.

The term "gel phase composition" as used herein, means the composition for making the pre-formed object being in a complete gel phase state during manufacturing.

The term "first surface" as used herein, means a lower surface of the pre-formed sheet during manufacturing, and after having been packaged.

The term "thickness" as used herein, means a thickness of a pre-formed sheet, wherein when the sheet is textured, the peaks of the texture are used for measuring the thickness.

The term "depth" as used herein, relates to a length in the thickness direction of a texture provided on the surface of a pre-formed sheet.

The term "frequency" as used herein, relates to the number of repeating non-planar topography per mm, the repetition of the non-planer topography providing a texture to the surface of a pre-formed sheet.

DETAILED DESCRIPTION

While the specification concludes with claims particularly pointing out and distinctly claiming the invention, it is believed that the present invention will be better understood from the following description.

Pre-formed Object

The pre-formed object provides structure and shape, allowing it to be handled and to suit treatment of a specific target area of the skin, hair or nails, or to be orally administered or consumed. It can also act as a reservoir or as a delivery vehicle for skin benefit agents and, when applied to the skin, hair or nails, by virtue of evaporation of a solvent from the pre-formed object, provide a cooling action to the object during use. The pre-formed object may be utilized for a cosmetic product, a pharmaceutical product, or a food product, by itself, or in combination with other materials.

The pre-formed object is free of a supporting substrate. The existence of a supporting substrate provides various advantages during manufacture, by giving flexibility and strength to the pre-formed object, and allowing ease of cutting the pre-formed object. The process of the present invention provides a suitable method of producing pre-formed objects without the aid of a supporting substrate.

The pre-formed objects have a plurality of surfaces that are continuously formed by pressing the sol phase composition against liners, and then cut, to form a pre-determined size and shape. The process herein can make any shape of object that is obtained by cutting a continuous flow of material. Objects that are advantageously made by the process herein include sheets, half-cylinders, and cylinders, and particularly such objects that are textured on at least one surface. When the pre-formed object is for topical application, the size and shape are adapted to conform to a desired target area which could be the nails or cuticles, the hair or scalp, a human face or part thereof, legs, hands, arms, feet, or human torso. The exact size and shape will depend upon the intended use and product characteristics.

Preferably, the pre-formed object has at least one surface textured. When the pre-formed object is a sheet, either or both of the first and second surfaces are textured. Preferably the first surface, or the lower surface, is textured. The texture for the surfaces herein are useful for the production process, the characteristic of the obtained product, or both, preferably for both. The texturing of the surface is useful for determining and thus controlling the flow of the sol phase composition when passing through the surface forming system and cooling step. The texturing of the surface may also provide various advantages to the obtained product. For example, the texturing may provide flexibility, ease of handling, more adhesion to the skin for dermal use, a matte appearance to the object, or distinct mouth feel for oral use. The particular characteristics for the cosmetic device herein are described below. The design, depth, and frequency of the texture is selected depending on the need of the process and character of the product. The texture is typically a regular repetition of pattern, and can be generalized across a certain area, provided only for a given area such as the peripheral, or provided different textures depending on the region. In a preferred pre-formed sheet embodiment, the texture is provided to the entire area of the first surface, more preferably, the texture is provided to the entire area of the first and second surfaces.

The pre-formed object made by the present invention is stable in more than one aspect. The pre-formed object has a suitable gel strength and a suitable flexibility, both characteristics having improved consistency over time at normal storage temperatures. Normal storage temperature typically refers to room temperature, preferably 25° C., however, when the pre-formed object is designed to be chilled or frozen on the shelf for display, stability should be assessed at the intended storage temperature.

When the pre-formed object is made of a composition that may go under syneresis, stability is also measured by the exudates produced by the pre-formed object over time. The pre-formed object made by the present invention produces less exudates than a composition made by, for example, injection molding.

The composition for making the pre-formed objects comprise, as essential components, a solvent and a gelling agent having a sol-gel transition point between about the melting point of the solvent and about the boiling point of the solvent. The weight percentage of components that make the composition are similar to that of the finally obtained pre-formed object, with slight increase or decrease occurring during the process, for example, loss of weight of water due to evaporation, or gain of weight of water due to hygroscopic components. For convenience, the weight percentage of components are referred to in view of the entire weight of the starting sol phase composition for making the pre-formed object.

Solvent

The pre-formed objects of the present invention comprise a solvent for the gelling agent. The solvent is selected so that a sol phase is made in combination with the gelling agent, wherein such sol phase transitions into a gel phase between the melting point and boiling point of the solvent. Typically the gelling agent is at least miscible in the solvent at sol phase state for eventually providing a uniform unilamellar pre-formed object. The amount and type of solvent is determined to provide a stable gel phase with the gelling agent, in view of the desired mechanical properties, particularly gel strength and flexibility, and also in view of the desired characteristic of the obtained product. Preferably, the solvent further acts as a plasticiser or softener for the pre-formed object.

or topical use, the pre-formed object comprises a hydrophilic solvent. The term "hydrophilic" as used in reference to solvents herein, means that the solvent is miscible with water, at least in a solvent to water ratio of 1 to 10, preferably 1 to 5. A topical acceptable, hydrophilic solvent is one which can be used in a pre-formed object to be applied against the skin without causing irritation and which is miscible with water. A highly preferred hydrophilic solvent is water itself. Other suitable hydrophilic solvents include lower alcohols such as ethanol, and polyhydric alcohols such as propylene glycol, butylene glycol, hexylene glycol, glycerin, sorbitol; polyethylene glycols of MW less than 30,000, preferably less than 10,000; and polypropylene glycols of MW less than 5,000, preferably less than 1,000. Advantageously, many of the polyhydric alcohols useful as hydrophilic solvents herein also function as humectants for the skin. Further, the hydrophilic solvent can assist in diffusion of skin benefit agents to the skin and, by evaporation from the pre-formed object, can also provide cooling, making the pre-formed object more comfortable to wear. Preferred in this latter respect are solvents which are liquid at 25° C. For topical use, preferably the solvent comprises water and at least one polyhydric alcohol, more preferably, the solvent consists essentially of water and polyhydric alcohol.

In a preferred embodiment for providing a cosmetic device, the pre-formed object comprises from about 10% to about 99.5% of water, more preferably from about 20% to about 95%, and yet more preferably from about 30% to about 90% of water. Still preferably, the pre-formed object further comprises from about 1.0% to about 50%, preferably from about 5% to about 45%, more preferably from about 10% to about 40% of polyhydric alcohol.

For oral administration use, the solvent is selected from the group hereinabove that are safe, and preferably pleasing, for oral consumption.

Gelling Agent

The pre-formed objects of the present invention comprises a gelling agent having a sol-gel transition point between about the melting point of the solvent and about the boiling point of the solvent. The gelling agent is selected in view of the solvent so that the pre-formed object can be manufactured at a safe and economical environment, and also to provide a pre-formed object that has a stable solid structure at normal storage temperature. When the solvent comprises water, the sol-gel transition point of the gelling agent is between 0° C. and 100° C., preferably between about 25° C. and about 80° C., more preferably between about 35° C. and about 70° C. The process herein forms the pre-formed object via a thermo transitioning point inherent of the solvent and the gelling agents. Gelling agents that do not form a sol phase in the solvent by elevated temperatures cannot be used in the process herein. Mixtures of gelling agents can be used.

The sol-gel transition point of the gelling agent is determined by providing a sol phase composition using the selected gelling agent and solvent, and periodically measuring its storage modulus (unit Pa, hereinafter described as G') and its loss modulus (unit Pa, hereinafter described as G") as the sol phase composition is cooled. The sol-gel transition point is the temperature where G' equals G". Such measurement methods are well known to those skilled in the art. It is known that gelling agents of natural origin, particularly gelling agents that are mixtures of natural polymers and have a viscoelastic nature, may provide a sol-gel transition point that is not very sharp, or may go through distinctive rheological transition points other than at the sol-gel transition point before reaching a complete, stable gel structure. The process of the present invention is particularly useful for providing a stable gel structure for pre-formed objects including such gelling agents.

The type and amount of gelling agent to be included in the pre-formed object is selected according to the desired characteristic and purpose of the product, depending on the properties of the gelling agent. Generally, more gelling agent will provide a more rigid pre-formed object. For providing food products or orally administrative products, the gelling agent must be edible and acceptable in taste and flavor. Many types of gelling agents are known in the art, including polymeric gellants and particulate based gellants such as various types of clays or other silicate based materials. Highly preferred herein are polymeric gelling agents that form 3-dimensional gel networks in combination with water. For providing cosmetic devices, the pre-formed object preferably comprises from about 0.5% to about 20%, more preferably from about 1% to about 10%, of gelling agent.

When the polymeric gel forming agents are natural in origin, the gels may undergo syneresis, to some degree. In the present invention, stability relates to pre-formed objects that undergo less syneresis, i.e., produces less exudate. Pre-formed objects made by the present process particularly produce less exudates compared to compositions made by injection molding.

The gelling agents herein may be water soluble or water insoluble, and selected according to the solvent. When the solvent is water or water-based, preferably the gelling agent is water soluble. Water insoluble polymeric gellants such as silicone materials e.g. organopolysiloxane resins, or block co-polymer thermoplastic elastomers, may be used in an appropriate solvent.

The water-soluble polymeric gellants for use in the present invention are selected from synthetic or natural polymers, and mixtures thereof. Preferred polymers for use herein are natural polymers, including gelatin, polysaccharides, and mixtures thereof. Preferred are polysaccharides. The term "polysaccharide" herein means a naturally occurring or synthetically produced, linear, branched or cross-linked polymer of monosaccharide units, which swells when dispersed in water at low concentrations and thickens the aqueous phase.

The polysaccharides for use in the pre-formed objects herein are preferably selected from red seaweed polysaccharides; glucomannans; galactomannans; fermentation polysaccharides, or derivatives thereof; brown seaweed polysaccharides; extracts of marine invertebrates; starch, or derivatives thereof; natural fruit extracts; plant fiber derivatives; kelp; natural plant exudates; and resinous gums; or mixtures thereof. The total polysaccharide level is controlled so that other optional components of the pre-formed object are not as tightly bound within the gel network and are available for diffusion.

When gelatin is used in the pre-formed objects herein, a high-molecular weight gelatin is combined with a low-molecular weight one to control the solubility. A gelatin having a low molecular weight of 20,000 or less has weaker gelling ability when used as the sole gelling agent.

Brown seaweed polysaccharides are isolated by extraction from various species of *Phaebophyceae*. Suitable brown seaweed polysaccharides for use herein include algin, alginic acid, ammonium alginate, calcium alginate, potassium alginate, sodium alginate, propylene glycol alginate, and mixtures thereof.

Red seaweed polysaccharides are isolated from marine plant species belonging to the class of *Rhodophyceae*. Red seaweed polysaccharides provide mechanical strength to the pre-formed object. Suitable red seaweed polysaccharides for use in the present invention include agar known in the industry under the (CTFA) trade designation as agar agar flake derived from various *Gelidium* plant species or closely related red algae commercially available as "Agar Agar 100" or "Agar Agar 150" from TIC Gums (Belcamp, Md., USA) or "Agar Agar K-100" from Gumix International Inc. (Fort Lee, N.J., USA); agarose commercially available as "Sea Plaque®" from FMC (Philadelphia, Pa., USA) and "Agarose Type 1-b" from Sigma—Aldrich Co. Ltd. (Poole, UK); carrageenan, comprising the fractions lambda-, iota- and kappa- which are the water extracts obtained from various members of the *Gigartinaceae* or *Solieriaceae* families, known in the industry under the (CTFA) trade designation as chondrus, commercially available as "Gelcarin® LA", "Seakem® 3/LCM", or "Viscarin® XLV", all from FMC (Philadelphia, Pa., USA); and furcellaran commercially available from Gum Technology Corporation (Tucson, Ariz., USA) and Continental Colloids Inc. (Chicago, Ill., USA), or mixtures thereof. Preferably, the red seaweed polysaccharide for use herein is selected from agar, agarose, kappa-carrageenan and furcellaran, or mixtures thereof.

Glucomannans are polysaccharides which comprise an essentially linear backbone of glucose and mannose residues. Glucomannans have short side branches attached to the linear backbone and acetyl groups are randomly present at the C-6 position of a sugar unit. The acetyl groups are generally found on one per six sugar units to one per twenty sugar units. Suitable glucomannans or derivatives thereof for use herein have a ratio of mannose to glucose of from about 0.2 to about 3. Preferred glucomannans for use herein include konjac mannan, which is the generic name for the flour formed from grinding the tuber root of the *Amorphophallus konjac* plant (elephant yam), commercially available under the trade name "Nutricol® konjac flour" from FMC (Philadelphia, Pa., USA); and deacetylated konjac mannan; or mixtures thereof.

Galactomannans are vegetable reserve polysaccharides which occur in the endosperm cells of numerous seeds of *Leguminosae*. The collective term "galactomannan" comprises all polysaccharides which are built up of galactose and mannose residues. Galactomannans comprise a linear backbone of (1→4)-linked β-D-mannopyranosyl units. To these rings are attached as branches, isolated galactopyranose residues by α-(1,6)-glucoside bonds. Galactomannans may in addition also contain minor amounts of other sugar residues. Suitable galactomannans for use herein are fenugreek gum; lucern; clover; locust bean gum known for example in the industry under the (CTFA) trade designation as carob bean gum, commercially available as "Seagul L" from FMC (Philadelphia, Pa., USA); tara gum commercially available from Starlight Products (Rouen, France) or Bunge Foods (Atlanta, Ga., USA); guar gum derived from the ground endosperms of *Cyamopsis tetragonolobus*, commercially available as "Burtonite V7E" from TIC Gums (Belcamp, Md., USA), "Jaguar C" from Rhone-Poulenc (Marietta, Ga., USA), or "Supercol" from Aqualon (Wilmington, Del., USA); and cassia gum commercially available from Starlight Products (Rouen, France), or mixtures thereof. Preferably, the galactomannans for use herein have an average one of every 1 to about 5 mannosyl units substituted with a (1→6)-linked-α-D-galactopyranosyl unit and are selected from guar gum, locust bean gum and cassia gum, or mixtures thereof.

Fermentation polysaccharides are polysaccharides which are commercially produced by the fermentation of microorganisms in a medium containing a carbon and nitrogen source, buffering agent, and trace elements. Suitable fermentation poly-saccharides or derivatives thereof, for use in the present invention include gellan gum known in the industry under the (CTFA) trade designation as gum gellan, a high molecular weight hetero polysaccharide gum produced by a pure-culture fermentation of a carbohydrate with *Pseudomonas elodea*, commercially available as "Kelcogel" from Kelco (San Diego, Calif., USA); xanthan gum which is a high molecular weight hetero polysaccharide gum produced by a pure-culture fermentation of a carbohydrate with *Xanthomonas campestris*, known in the industry under the (CTFA) trade designation as xanthan, commercially available for example as "Keltrol CG 1000/BT/F/GM/RD/SF/T/TF", from Calgon (Pittsburgh, Pa., USA), or "Kelzan" from Kelco (San Diego, Calif., USA); natto gum; pullulan; rhamsan gum; curdlan; succinoglycan; welan gum; dextran, commercially available as "Sephadex G-25" from Pharmacia Fine Chemicals (Piscataway, N.J., USA) and derivatives thereof; and sclerotium gum, commercially available as "Amigel" from Alban Muller International (Montreil, France), or mixtures thereof. Preferred fermentation polysaccharides or derivatives thereof are selected from gellan gum and xanthan gum, or mixtures thereof. More preferably the fermentation polysaccharide or derivative thereof is xanthan gum.

Extracts of marine invertebrates can also be used. Polysaccharides derived from marine invertebrates, specifically the exoskeleton of such invertebrates, consist chiefly of N-acetyl-D-glucosamine residues. Examples of such polysaccharides suitable for use herein include chitosan, commercially available for example as "Marine Dew" from Ajinomoto (Teakneck, N.J., USA); and hydroxypropyl chitosan commercially available for example as "HPCH Liquid" from Ichimaru Pharcos (Yamagata Gun Gifu-Pref, Japan) and derivatives; or mixtures thereof.

Starches are polysaccharides which consist of various proportions of two glucose polymers, amylose and amylopectin. Suitable materials for use herein include starch, amylopectin and dextrin, commercially available as "Nadex 360" from National Starch (Bridgewater, N.J., USA), and derivatives or mixtures thereof. Examples of natural fruit extracts suitable for use herein include pectin, arabian and mixtures thereof. A suitable example of a plant fiber derivative for use herein is cellulose. Suitable polysaccharides obtained from natural plant exudates for use herein include karaya, tragacanth, arabic, tamarind, and ghatty gums, or mixtures thereof. Examples of resinous gums suitable for use herein include shellac gum, which is obtained from the resinous secretion of the insect *Laccifer* (*Tachardia*) *lacca*, damar gum; copal gum and rosin gum; or mixtures thereof.

Natural and synthetic polymeric gelling agents that form gels in combination with other substances may also be used as a gelling agent in combination with other thermo-forming gelling agents, so long as the gel phase forming can been synchronized. They may be chemically cross linked. Some gelling agents form gels in combination with substances such as sugar, alcohol, or mono- or multi-valent salts. Mono- or multi-valent salts may additionally act as gel strengthening agents imparting added strength to the pre-formed objects herein. Suitable cations for such salts can be selected from potassium, sodium, ammonium, zinc, aluminium, calcium and magnesium ions, or mixtures thereof. Suitable anions associated with the aforementioned cations may be selected from chloride, citrates, sulfate, carbonate, borate and phosphate anions, or mixtures thereof.

Physical cross linking refers to polymers having cross links which are not chemical covalent bonds but are of a physical nature such that there are areas having high crystallinity or areas having a high glass transition temperature. Such cross linked polymers may also be used. Preferably, the polymer is chemically cross linked thermally. In addition when chemical cross links are formed in the system, a polyfunctional cross linker and/or a free radical initiator may be present in the premix to initiate the cross linking upon irradiation.

Preferably, the pre-formed objects herein comprise a mixture of water-soluble polymeric gelling agents of natural origin. A preferred water-soluble polymeric gelling agent mixture herein may comprise a polysaccharide and a non-ionic water-soluble polymer or, alternatively, it may comprise two polysaccharides. More preferably, the water-soluble polymeric gel forming agent is a polysaccharide mixture, wherein the polysaccharide mixture comprises (1) at least one red seaweed polysaccharide; brown seaweed polysaccharide; or mixtures thereof; and (2) at least one fermentation polysaccharide; galactomannan; glucomannan; natural plant exudate; or natural fruit extract; and derivatives or mixtures thereof. Even more preferably, the water-soluble polymeric gel forming agent of the pre-formed objects of the present invention is a polysaccharide mixture comprising (1) at least one red seaweed polysaccharide; and (2) at least one fermentation polysaccharide; glucomannan; or galactomannan; and derivatives or mixtures thereof.

In a preferred embodiment, the water-soluble polymeric gel forming agent of the present invention is a polysaccharide mixture, comprising a red seaweed polysaccharide and a glucomannan or a galactomannan. The ratio of red seaweed polysaccharide to glucomannan or galactomannan in the polysaccharide mixture is preferably from about 20:1 to about 1:5 and more preferably from about 10:1 to about 1:2. Without being limited by theory, it is believed that gel compositions herein form 3-dimensional networks or matrices which bind or encapsulate other ingredients of the composition. Further, it has been found that this highly preferred polysaccharide mixture has a sol-gel transition point at between about 35° C. and about 70° C. that is not very sharp, and has a second distinctive theological transition point at between about 20° C. and about 50° C. It has been found that the composition comprising the highly preferred polysaccharide mixture forms a stable gel structure after being cooled below such second transition point. The process of the present invention is particularly useful for such highly preferred polysaccharide mixture. In a highly preferred embodiment, the gel phase composition is cooled well below the second transition point in the cooling process. By cooling the gel phase composition to such extent, a pre-formed object having stability in terms of gel strength, flexibility, and reduced exudates is obtained.

Cosmetic Device

In a highly preferred embodiment, the pre-formed object of the present invention is a sheet-like cosmetic device for delivering skin benefit agents to the skin hair or nails. Herein, the term "pre-formed sheet" is used to describe such sheet-like pre-formed object. A pre-formed sheet is a preferable embodiment of the pre-formed object herein.

The cosmetic device of the present invention comprises a pre-formed sheet made by the process described below, and may further comprise a coating composition. The coating composition may be included in the same package as the pre-formed sheet to reach equilibrium in the package. Such application step of the coating composition onto the pre-formed sheet may be disposed in a continuous manner of making the cosmetic device.

Cosmetic devices according to the present invention are generally of a size such that each surface has an area of from about 0.25 $cm^2$ to about 1,000 $cm^2$, preferably from about 1 $cm^2$ to about 300 $cm^2$. Surface area refers to that of a flat plane having the same boundary as the surface i.e. ignoring any surface texturing present.

The cosmetic devices herein can be, for example, square, circular, semicircular, rectangular, oval, rings, crescents, teardrops or other more complex shapes which may be composites of these, for covering areas such as the eye area, eye lids, the nose, the mouth area, the forehead, the chin, the entire contour of the face, or combinations thereof.

Coating Compositions

In the pre-formed sheet of the present invention, the first surface is at least partially coated with a discrete coating composition comprising at least one skin benefit agent for the skin, hair or nails. By "discrete" coating composition is meant one that is applied to the pre-formed sheet as a distinctly different composition, in particular one having a different chemical constitution which is separately prepared from the pre-formed sheet and is laid down as a separate layer, before, after or at the same time as the formation of the pre-formed sheet. The coating composition allows more efficient delivery of skin benefit agents to the skin and affords greater formulation flexibility.

The coating composition comprises at least one skin benefit agent for the skin, hair or nails. Preferably, the pre-formed sheet and the coating composition each comprise at least one skin benefit agent in common. In this way, whilst the coating composition can rapidly provide a skin benefit agent to the target area, the pre-formed sheet can act as a reservoir for the skin benefit agent or inhibit the pre-formed sheet from absorbing the skin benefit agent from the coating composition.

Skin Benefit Agents

In a highly preferable embodiment, the cosmetic device of the present invention comprises a coating composition which comprises at least one skin benefit agent for the skin hair, or nails. The solid pre-formed sheet preferably also comprises one or more of such skin benefit agents. The term "skin benefit agent" as used herein, means an active ingredient which provides a cosmetic and/or therapeutic effect to the area of application on the skin, hair, or nails. The skin benefit agents useful herein include anti-acne agents, emollients, non-steroidal anti-inflammatory agents, topical anaesthetics, artificial tanning agents, antiseptics, anti-microbial and anti-fungal actives, skin soothing agents, sunscreening agents, skin barrier repair agents, anti-wrinkle agents, anti-skin atrophy actives, lipids, skin lightening agents, sebum inhibitors, sebum inhibitors, skin sensates, protease inhibitors, skin tightening agents, anti-itch agents, hair growth inhibitors, desquamation enzyme enhancers, anti-glycation agents, and mixtures thereof.

In general, the coating compositions of the present invention comprise from about 0.01% to about 60%, preferably from about 0.1% to about 40% and most preferably from about 0.5% to about 30% by weight of the coating compositions of at least one skin benefit agent, or mixtures thereof.

Preferred examples of skin benefit agents useful herein include those selected from the group consisting of ascorbic acid and derivatives thereof, salicylic acid, niacinamide, panthenol, tocopheryl nicotinate, benzoyl peroxide, 3-hydroxy benzoic acid, flavonoids (e.g., flavanone, chalcone), farnesol, phytantriol, glycolic acid, lactic acid, 4-hydroxy benzoic acid, acetyl salicylic acid, 2-hydroxybutanoic acid, 2-hydroxypentanoic acid, 2-hydroxyhexanoic acid, cis-retinoic acid, trans-retinoic acid, retinol, retinyl esters (e.g., retinyl propionate), phytic acid, N-acetyl-L-cysteine, lipoic acid, tocopherol and its esters (e.g., tocopheryl acetate), azelaic acid, arachidonic acid, tetracycline, ibuprofen, naproxen, ketoprofen, hydrocortisone, acetorninophen, resorcinol, phenoxyethanol, phenoxypropanol, phenoxyisopropanol, 2,4,4'-trichloro-2'-hydroxy diphenyl ether, 3,4,4'-trichlorocarbanilide, octopirox, lidocaine hydrochloride, clotrimazole, miconazole, ketoconazole, neomycin sulfate, theophylline, and mixtures thereof.

For cosmetic methods of treatment of the skin, hair or nails, the cosmetic skin benefit agent is preferably selected from anti-wrinkle and anti-skin atrophy actives, anti-acne actives, artificial tanning agents and accelerators, emollients, humectants, skin repair actives, skin barrier repair aids, skin lightening agents, skin sensates, skin soothing agents, lipids, sebum inhibitors, sebum stimulators, sunscreening agents, protease inhibitors, skin tightening agents, anti-itch ingredients, and desquamation enzyme enhancers, or mixtures thereof.

The pH of the pre-formed sheets and coating compositions herein is preferably from about 3 to about 9, more preferably from about 4 to about 8. The pH may be selected depending on the activity of the skin benefit agent.

Process of Manufacturing the Pre-Formed Object

The process for making a pre-formed object having a plurality of surfaces of the present invention relates to a continuous line process comprising the steps of:
  (1) providing a sol phase of the composition comprising a solvent and a gelling agent having a sol-gel transition point between about the melting point of the solvent and about the boiling point of the solvent;
  (2) forming surfaces of the sol phase composition by passing through a surface forming system, the surface forming system pressing the sol phase composition between a plurality of liners;
  (3) cooling the sol phase composition into a gel phase; and
  (4) cutting the gel phase composition;
  wherein the pre-formed object is free of a supporting substrate.

The process of the present invention relates to forming the pre-formed object via cooling. The process herein is suitable for providing a continuous flow of material for making the pre-formed object, and thus can be suitably applied to large scale manufacturing. The process herein may be used for making pre-formed objects comprising any gelling agent having a sol-gel transition point, however, is particularly useful for gelling agents that do not have a sharp sol-gel transition point, or have rheological transfer points other than the sol-gel transition point. In this respect, the process herein is particularly useful for making pre-formed objects comprising a mixture of gelling agents of natural source.

The present invention further relates to a continuous line process for making a pre-formed sheet having a first surface and a second surface comprising the steps of:
  (1) providing a sol phase composition of the pre-formed sheet comprising:
    (a) from about 10% to about 99.5% water; and
    (b) from about 0.5% to about 20% polysaccharide gelling agent having a sol-gel transition point between about 25° C. and about 80° C.;
    wherein the sol phase composition is heated to a temperature of at least 5° C. higher than the sol-gel transition point;
  (2) pre-cooling the sol phase composition to a temperature of between 0° C. and 5° C. higher than the sol-gel transition point;
  (3) forming the first and second surfaces by pressing the sol phase composition between two liners, the two liners being supplied by two counter-rotating rollers facing each other, wherein the rollers further comprise cooling means, wherein the two liners further provide textures to the first and second surfaces;
  (4) cooling the sol phase composition into a gel phase by cooling to no higher than 20° C.; and
  (5) cutting the gel phase composition by a die;
  wherein the pre-formed sheet is free of a supporting substrate and the pre-formed sheet has a flex angle of from about 15° to about 80°.

In a preferred continuous line process, all of the manufacturing steps from sol phase making to finished product packaging are disposed in a continuous line with speed buffer means and transfer means to carry material to a different line, as necessary.

The present invention further relates to a process for providing a packaged cosmetic device comprising: a pre-formed sheet and a coating composition comprising a skin benefit agent; comprising the steps of:
(1) providing a unsealed package;
(2) applying the coating composition in the package;
(3) placing the pre-formed sheet in the package; and
(4) sealing the package;

wherein the steps are in communication with each other to provide a continuous line process.

As the preferred pre-formed sheets herein utilize water as the solvent, the pre-formed sheet is relatively vulnerable to change of humidity, particularly excessive or rapid drying. Drying beyond a certain extent, depending on the composition, will decompose or deform the pre-formed object by destroying its gel structure. Therefore, in the process herein, it is advantageous to dispose the packaging means for the cosmetic device such that the pre-formed sheet is immediately packaged and sealed after production.

Figure 1:
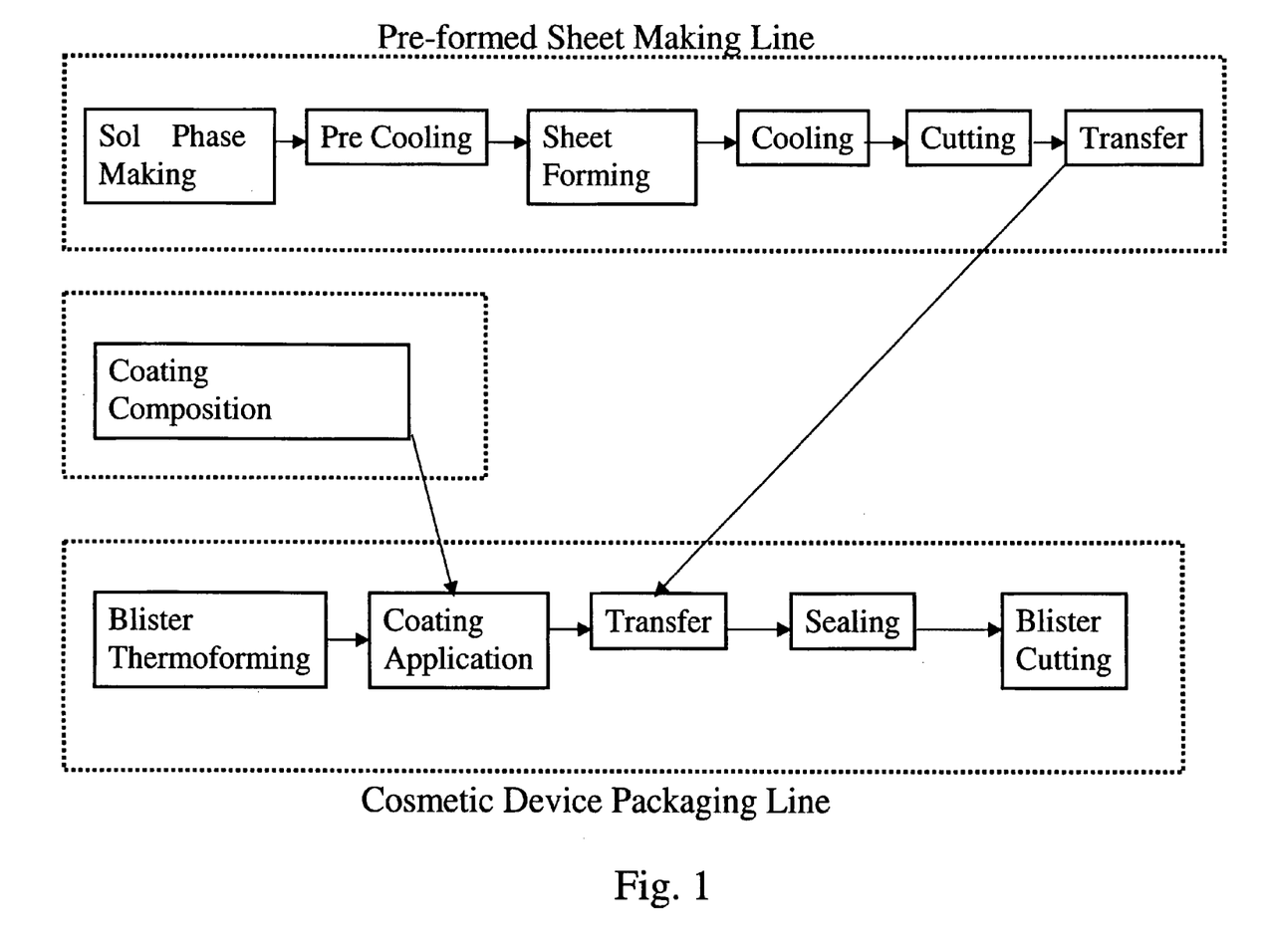
FIG. 1 is a schematic view of a preferred embodiment of the process of the present invention.

FIG. 1 schematically depicts a process, in functional perspectives, for making a preferred cosmetic device embodiment comprising a pre-formed sheet having a composition selected from one of Table 1 and a coating composition selected from one of Table 2, wherein the cosmetic device is packaged in a blister package.

While the process of the present invention may be used to form any number of surfaces, the process for making a pre-formed sheet having a first surface and a second surface for the preferred cosmetic device embodiment is illustrated herein.

TABLE 1

Compositions for Pre-formed Sheet

| Ingredient | % w/w | % w/w | % w/w | % w/w |
|---|---|---|---|---|
| Agarose | 0.3 | 0.8 | 1.6 | 1.5 |
| Agar | 0.60 | — | — | — |
| Kelgum (Kelco)[1] | — | 0.5 | 0.8 | 0.75 |
| Keltrol T (Kelco)[1] | 0.2 | — | — | — |
| Locust Bean Gum | 0.2 | — | — | — |
| Niacinamide | — | 5.0 | 8.0 | 10.0 |
| D-Panthenol | 5.0 | — | 2.0 | 1.0 |
| Glycerin | 10.0 | 15.0 | 10.0 | 10.0 |
| Disodium EDTA | — | 0.10 | 0.10 | 0.10 |
| Butylene Glycol | — | 5.0 | — | — |
| Hexylene Glycol | 3.0 | — | 5.0 | 5.0 |
| Ethyl Paraben | 0.20 | 0.15 | 0.15 | 0.15 |
| Water | to 100% | to 100% | to 100% | to 100% |

TABLE 2

Coating compositions

| Ingredient | % w/w | % w/w | % w/w | % w/w | % w/w |
|---|---|---|---|---|---|
| Kelgum (Kelco)[1] | 0.1 | — | — | — | — |
| Keltrol T (Kelco)[1] | — | 0.5 | 0.9 | — | 0.8 |
| Locust bean gum | 0.4 | — | — | — | — |
| Polyacrylamide, isoparaffin & laureth-7 | — | — | — | 2.75 | — |
| Niacinamide | 5.0 | — | 8.0 | 3.5 | 10.0 |
| D-Panthenol | — | 5.0 | 2.0 | 2.0 | 1.0 |
| Glycerin | — | 5.0 | 10.0 | 9.0 | 10.0 |
| Disodium EDTA | 0.10 | 0.1 | 0.1 | 0.1 | 0.1 |
| Butylene glycol | — | 5.0 | — | — | — |
| Hexylene glycol | — | — | 5.0 | — | 5.0 |
| Tospearl ™ 145[2] | — | — | 6.0 | 1.0 | 7.5 |
| DC 2-1559 emulsion[3] | — | — | 3.0 | 4.0 | 3.0 |
| Magnesium ascorbyl phosphate | 3.0 | — | — | — | — |
| Tocopheryl acetate | 0.5 | — | — | 0.75 | — |
| PEG-60 hydrogenated castor oil | 1.50 | — | — | — | — |
| Cetyl alcohol | — | — | — | 1.5 | — |
| Stearyl alcohol | — | — | — | 1.0 | — |
| Lonzaine ™ 16SP[4] | 0.47 | — | — | — | — |
| Tinoderm ™ E[5] | — | — | — | — | 10.0 |
| Sucrose cocoate and sorbitan stearate[6] | — | — | — | 1.0 | — |
| Isohexadecane | — | — | — | 2.0 | — |
| Isopropyl isostearate | — | — | — | 1.0 | — |
| SEFA cottonate | — | — | — | 1.0 | — |
| Petrolatum | — | — | — | 3.0 | — |
| Water, fragrance, preservatives | | | to 100% | | |

[1]Kelgum and Keltrol T are, respectively, a 1:1 mixture of xanthan gum and locust bean gum; and xanthan gum, supplied by Kelco, San Diego, CA, USA.
[2]Polymethylsilsesquioxane from Toshiba
[3]Dimethicone, dimethiconol, laureth-4, laureth-23, and water; from Dow Corning
[4]Water and cetyl betaine from Lonza
[5]Water, tocopheryl acetate, polysorbate 80, caprylic/capric triglyceride and lecithin from CIBA
[6]Arlatone 2121 from ICI Referring to FIG. 1, the process of the present invention for making the pre-formed sheet is generally described as the pre-formed sheet making line. The coating composition is prepared separately, and supplied to the cosmetic device packaging line, wherein the unsealed blister package receives the coating composition, followed by receiving the transferred pre-formed sheet, to make a cosmetic device. The cosmetic device is then sealed. The blister package is typically supplied in plurality as a continuous sheet of thermoformed material. After the cosmetic device is received and sealing is provided, the continuous packaging material is cut into unit application forms. The pre-formed sheet making line is depicted in detail in FIG. 2.

Figure 2:
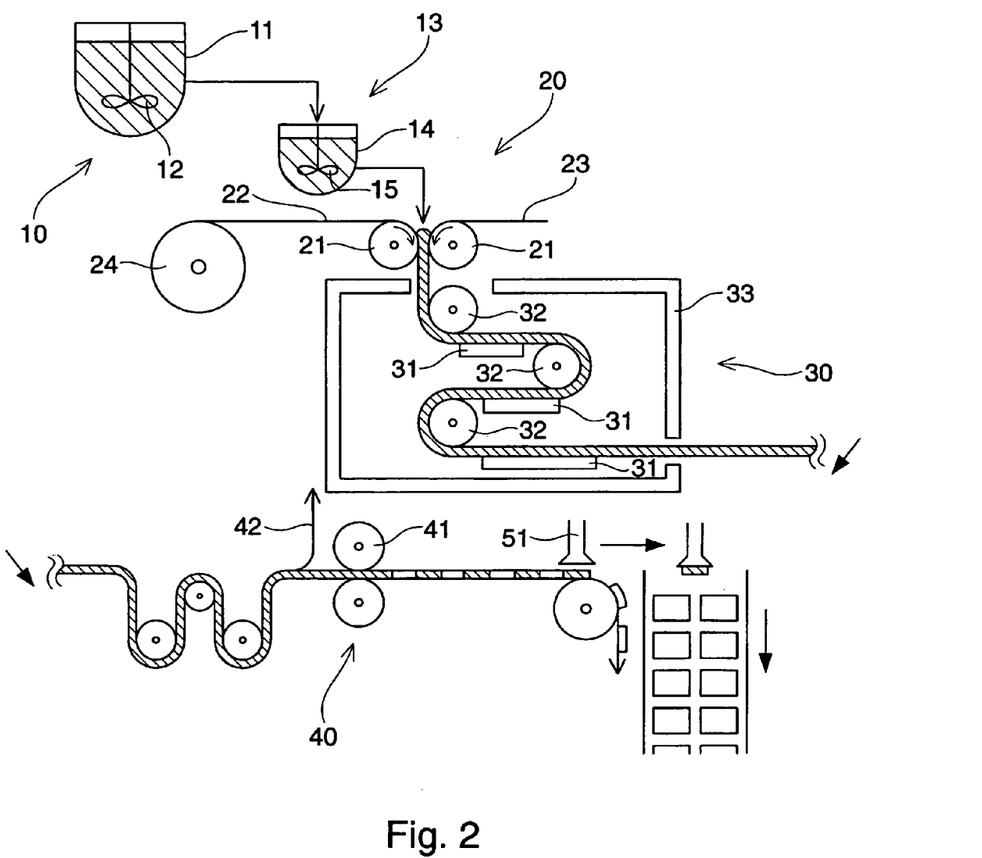
FIG. 2 is another schematic view of a preferred embodiment of the process of the present invention.

Referring to FIG. 2, the process of the present invention starts by providing a sol phase of the composition, in this embodiment, the composition of one of Table 1. The sol phase making step (10) is typically conducted by mixing the components of the pre-formed sheet in a tank (11) at a temperature well above the sol-gel transition point, preferably at least 5° C. higher than the sol-gel transition point. In this embodiment, the sol phase making is conducted at elevated temperature with the aid of stirring (12). The stirring is kept to a degree so that the structures of the polymeric gelling agents per se are not destroyed.

Preferably, the sol phase composition is pre-cooled before being sent to the sheet forming system. In the pre-cooling step (13), the sol phase composition is cooled to a temperature still above, but closer to the sol-gel transition point, for example by means of placing in a pre-sheet forming tank (14). Preferably, the sol phase composition is cooled to a temperature of between 0° C. and 5° C. higher than the sol-gel transition point. It has been found that, with the aid of stirring (15), the sol phase composition can retain the sol phase at the sol-gel transition point temperature.

The pre-cooled sol phase composition is then delivered to the surface forming system, in this embodiment, the sheet forming system (20). The sheet forming system is preferably a mechanical pressuring of the sol phase composition against two hard surfaces facing each other, such as counter-rotating rollers or plates facing each other. Passing of the sol phase system through counter-rotating rollers are preferred in that it allows continuous flow of the line. When a pair of opposing plates is used for the surface forming system, the continuity of flow can be provided by allowing intervals during the pressing of a given area for a determined period of time. In this embodiment, the sol phase composition is poured at a controlled rate between the first liner (22) and the second liner (23) supplied by two counter-rotating rollers (21) which supply the liners.

Figure 3:
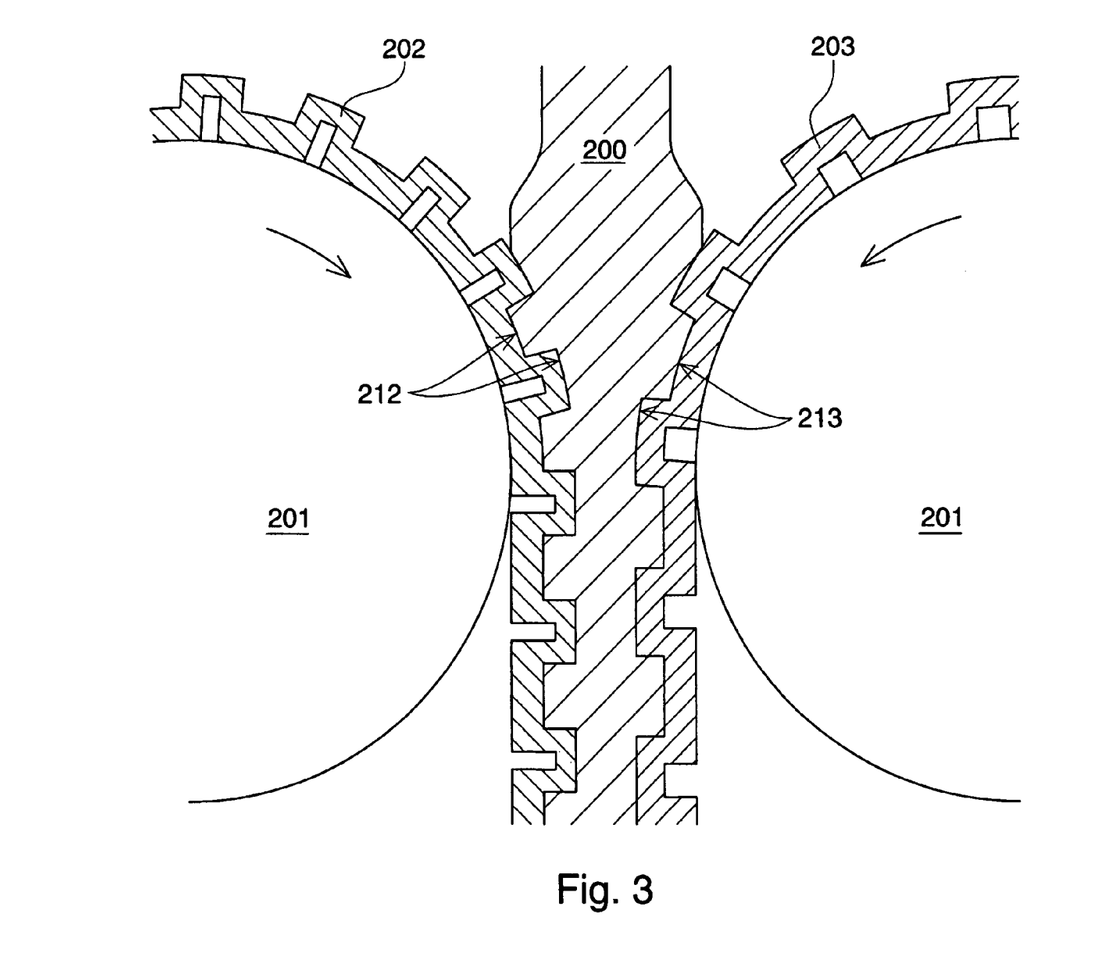
FIG. 3 is a schematic view of a preferred embodiment of the surface forming system of the present invention.

FIG. 3 is a schematic view of a preferred embodiment of the surface forming system of the present invention, with the thickness of the liners and depths of textures inflated. Referring to FIG. 3, the sol phase composition (200) which is in a fluid state is directed between the first liner (202) and the second liner (203), wherein mechanical pressure is applied to the sol phase composition by the rotating action of the rollers. In order to direct the sol phase composition to the engaging point of the rotating rollers, the sol phase composition may be poured at the engaging point, or poured at one of both of the liners to be delivered to the engaging point. In this embodiment, the sol phase composition travels vertically in the surface forming system, however, the surface forming system may also be configured horizontally. Preferably the first liner is textured to provide a non-planer topography, more preferably the second liner is further textured to provide a non-planer topography. In this embodiment, both liners provide textures of regular frequency. Such textures are transferred to the sol phase composition via mechanical pressure applied to the sol phase composition (212, 213), and preferably by further cooling of the sol phase composition while passing the liners in contact with the counter-rotating rollers, wherein the rollers (201) encompass a cooling means, typically a continuous running of cold water. As the liners are unwound from the counter-rotating rollers, the partially formed sol phase composition which is adhered to the two liners are released from the pressure of the counter-rotating rollers, to travel to the next step.

The liners herein are thin enough to provide effective cooling, while thick enough to retain its mechanical strength and texture definition through the process. The material for the liners are selected in view of heat conductivity, rigidity, elasticity, adhesion to the sol phase composition, and inertness of the gel phase composition. In this embodiment, preferred liners are made of polyethylene and have a thickness of from about 10 µm to about 50 µm. Referring to FIG. 2, when textured liners are used, the liners may be formed to the desired texture by a pressing against an embossing roller (24) with the aid of heat prior to supplying to the surface forming system. The embossing process for the liners may be conducted discontinuous to the line process herein. The same may be applied to the second liner.

The preferred surface forming system herein is advantageous in many ways for providing pre-formed sheets having textured surfaces, free of a supporting substrate. For example, the sol phase composition would be effectively cooled so that at least the surfaces of the composition in contact with the liners would quickly transition to a harder state or partial gel phase, thereby ensuring well defined textures at the surfaces. Further, control of the overall line flow of the composition is improved, as the gelled or solidified surface would be less susceptible to process vibration and movement of the liner. Further, the entire process line can be rationalized, as less subsequent cooling would be necessary, thereby leading to shorter lines or faster process. The speed in which the sol phase composition passes the surface forming system is carefully adjusted so that the surfaces are soft enough to be textured, but having solid enough surfaces after leaving the system.

In the process herein, the composition which is partially gelled or gelled only in local areas, particularly the surfaces, are defined as a sol phase composition. It is typical that the composition leaving the surface forming system is still a sol phase composition, even if the surface of the composition is below the sol-gel transition point.

The process of the present invention provides stable pre-formed sheets having a thickness of about 0.1 mm to about 5 mm with relatively deep texture depths, as deep as about 10 µm to about 500 µm, depending on the thickness of the pre-formed sheet. In a particularly preferred embodiment, the pre-formed sheet has a thickness of about 0.5 mm to about 2.0 mm, and a texture depth of from about 50 µm to about 200 µm at the first and second surfaces. Such specific texturing of the surfaces may provide various advantages to the cosmetic device comprising the pre-formed sheet, which are described below.

Referring to FIG. 2, the partially solidified sol phase composition, which may be partially gelled, is then directed to the cooling system (30) for completely transitioning the composition into a gel phase. In this embodiment, the cooling is achieved by direct cooling such as by cooling plates (31) and chilled rollers (32), and additionally by indirect cooling such as by placing the line in a cooling chamber (33). In this embodiment, the composition is cooled to the extent the entire sheet is transitioned to a complete stable gel phase.

The speed of cooling at the surface forming step and the cooling step are important factors of the process herein for obtaining a stable gel phase for the pre-formed sheet. The speed will depend on the composition for the pre-formed sheet, particularly on the rheological behaviors of the composition during the process. For this embodiment, the rate of cooling is preferably from about 5° C. to about 100° C. per minute, more preferably from about 10° C. to about 50° C. per minute. Generally, the speed of cooling is much faster when the pre-formed sheet is made by injection molding processes. Particularly for pre-formed sheet embodiments that use natural gelling agents, the slower cooling achieved in the process herein is beneficial for providing a stable product.

Figure 4:
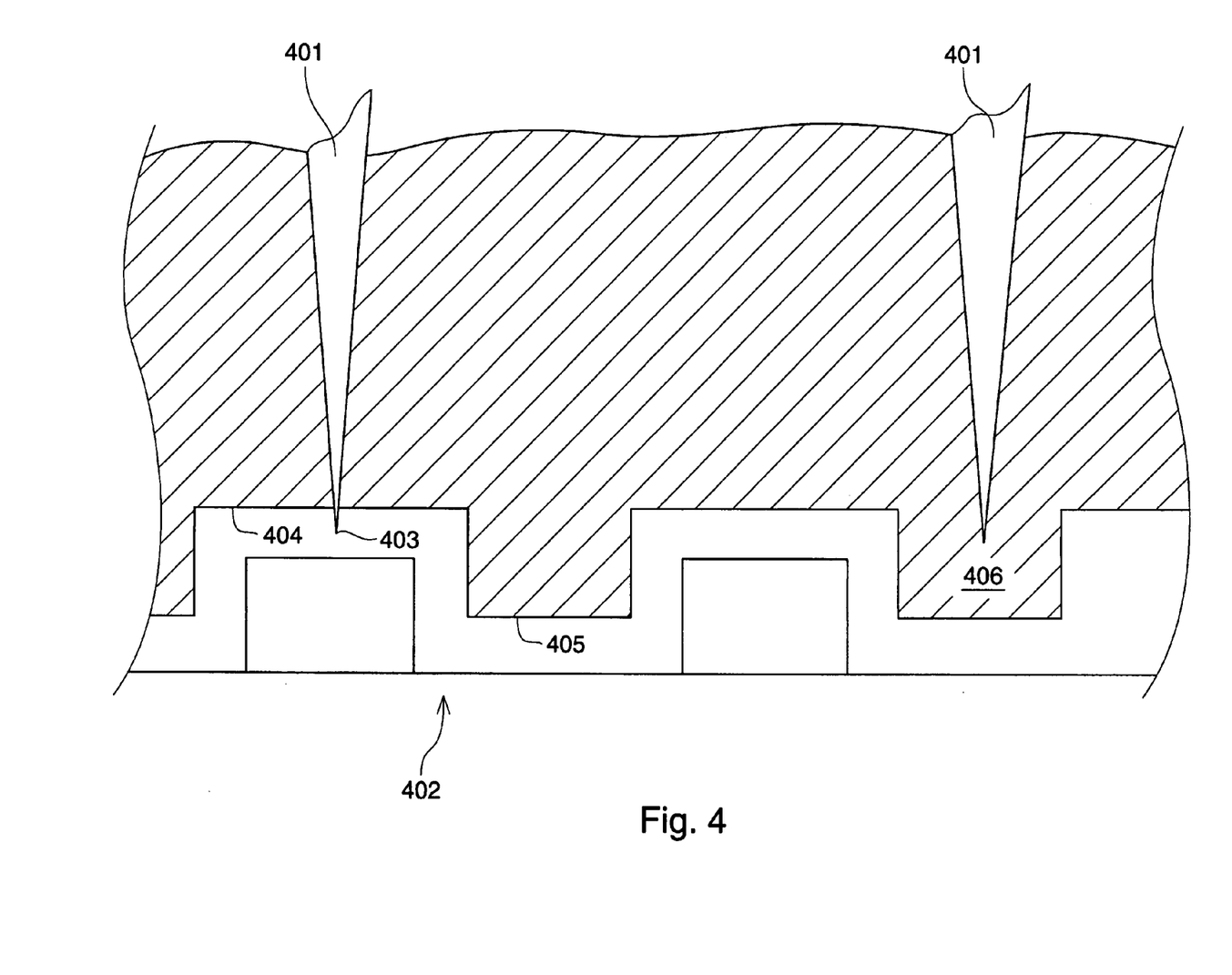
FIG. 4 is a schematic view of a preferred embodiment of the cutting system of the present invention.

The gel phase composition thus obtained is then cut (40) into its predetermined size and shape to obtain the pre-formed sheet. The liner in contact with the second surface may be removed (42) prior to the cutting step. The liner in contact with the first surface is preferably kept intact until after the cutting step. The cutting can be conducted by any means known in the art. For effective cutting in a continuous line process, cutting is preferably conducted by vertical movement of a die, preferably by rotating a roller having the dies disposed on the surface (41). The preferred cutting step of the present invention is also advantageous for effectively providing pre-formed sheets having relatively deep texture depths on the first surface. In the preferred embodiment for making a cosmetic device, both surfaces of the pre-formed sheet are textured in a regular pattern.

FIG. 4 is a schematic view of a preferred embodiment of the cutting system of the present invention, with thickness of the liners inflated. Referring to FIG. 4, the blades of the die (401) enter from the second surface toward the edge of the first surface (402) for vertically cutting the pre-formed sheet. The extent of cutting is so controlled that the edge of the blade of the die (403) reaches beyond the bottom (404) of the texture of the first surface, however, does not reach beyond the peak (405) of the texture of the first surface. It has been surprisingly found that, even when the edge of the die blade does not completely cut the thickness of the sheet such as in the area shown as 406, such area can be cut without additional process steps. The area 406, where the die blade does not reach, is cut by the shear applied by the movement of the die blade, or by forcing the pre-formed sheet to tear off upon transferring the pre-formed sheet, or both, without affecting the shape or stability of the obtained pre-formed sheet.

Referring to FIG. 2, the finally obtained pre-formed sheet is further transferred for packaging by, for example, an arm with suction means (51) which removes the pre-formed sheets away from the liner in contact with the first surface. Effective and convenient packaging can be conducted by releasing the sucked pre-formed sheet and placing into the package, followed by sealing of the package. In this embodiment, the pre-formed sheet is placed into a blister package in this manner, wherein the first surface remains the lower surface in the package, the second surface to face the sealing of the package.

The coating composition for the cosmetic device is separately made. A variety of methods are suitable for applying the coating to the pre-formed sheet in order to form the finished cosmetic device. For example, the coating may be applied directly to the pre-formed sheet e.g. dispensed via a pipette to provide 'dots' of coating or spread with a brush to provide an uniform layer. Alternatively, the coating may be applied using screen printing techniques or via an extrusion process. The coating may also be applied to the pre-formed sheet via an indirect process. Referring to FIG. 1, in this embodiment, the coating composition is applied to a surface of the blister package, and then the pre-formed sheet is placed on top of the coating composition. A variety of methods may be used to apply the coating to the packaging material. These include air atomised spraying of the coating, dot deposition of the coating via a nozzle cosmetic device or an electrofluidic coating process of the type used in ink jet printing. A preferred method is dot deposition of the coating composition into a packaging tray using nozzles, swirling the nozzles to provide an uniform layer of coating, then pressing the pre-formed sheet onto the top of the coating composition.

Figure 7:
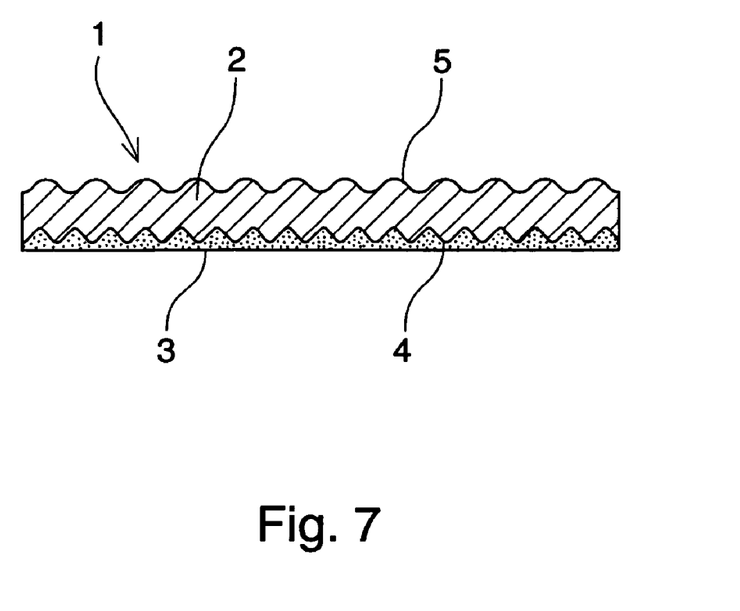
FIG. 7 is a sectional view of a preferred embodiment of the cosmetic device of the present invention.

The packages for the cosmetic device embodiment herein is made of materials which have low water vapor permeability to minimize drying out of the cosmetic device during storage. Any suitable material can be used for the packaging such as plastics materials and foil laminates. This protection can be provided by a substrate or by a release liner such as a plastic film, which provides easy release upon using the cosmetic device. An embodiment of the pre-formed sheet for the cosmetic device made by the process of the present invention is shown in perspective in FIG. 5 wherein the first surface is shown on top. The pre-formed sheet is broadly crescent shaped, of dimensions such that a notional rectangle of 4 cm×2 cm bounds the crescent, and the first surface has repeating diamond shaped convexes which provide a distinct texture. Provided in section view as in FIG. 7, the cosmetic device (1) comprises a pre-formed sheet (2) and coating composition (3) on a first surface (4) of the pre-formed sheet. The pre-formed sheet is generally flat having a uniform thickness. The pre-formed sheet has a second surface (5) opposed to the first surface (4). The pre-formed sheet by the process herein does not have distinct rims at the peripheral. However, it has been surprisingly found that, even without the rims, the pre-formed sheet of the present invention provides enough strength to the cosmetic device for handling at regular conditions.

Figure 8:
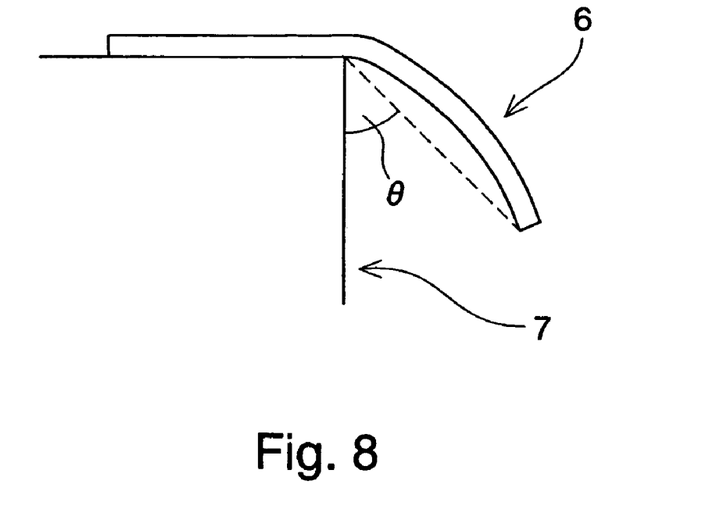
FIG. 8 is a schematic view of a set up for measuring flex angle.

Key parameters for evaluating the physical characteristics of the obtained cosmetic device are gel strength and flexibility. Flexibility for the cosmetic device herein is measured by how much the device bends under its own weight when it overhangs an edge at its most flexible surface. Minimum required gel strength is confirmed by checking if the device does not rupture under its own weight when overhanging. A 4 cm by 2 cm rectangular, test strip of the pre-formed sheet is prepared. For cosmetic devices of the present invention which comprise the pre-formed sheet and a coating composition, the test strip should be evenly coated with the coating composition at a rate of 0.015 g/cm$^2$, and should be measured at 25° C. The strip, coated first surface uppermost, is supported on a flat surface, having a rectangular edge so that 2 cm of the 4 cm length of the strip can overhang without obstruction. The arrangement is shown schematically in FIG. 8. Test strip (6) (coating composition not shown) overhangs the vertical edge of solid support (7), whose upper surface is horizontal. The angle θ of overhang from the vertical is measured by drawing a straight line (shown as a dashed line in FIG. 8) from the tip of the gel sheet to the edge of the support. This can conveniently be done from a photograph. The test strip should not rupture upon overhanging. The angle of overhang, θ, is the flex angle of the composition. The test strip should have a flex angle of from about 15° to about 80°, preferably from about 25° to about 75° and more preferably from about 40° to about 60°.

The present invention further relates to a cosmetic device comprising:
 (1) a pre-formed sheet comprising:
  (a) from about 10% to about 99.5% water; and
  (b) from about 0.5% to about 20% polysaccharide gelling agent having a sol-gel transition point between about 25° C. and about 80° C.;
 wherein the pre-formed sheet is free of a supporting substrate, has a thickness of from about 0.1 mm to about 5 mm, preferably from about 0.5 mm to about 2.0 mm and a first surface and a second surface, the first surface having a repeating texture having a depth of from about 10 μm to about 500 μm, preferably from about 50 μm to about 200 μm at a frequency of from about 0.2 to about 1 per mm, preferably from about 0.3 to about 0.7 per mm; wherein the depth of the texture is at least about 10% of the thickness of the pre-formed sheet; and (2) a coating composition comprising a skin benefit agent and having a viscosity of from about 1000 mPa·s to about 30,000 mPa·s, preferably from about 5000 mPa·s to about 15,000 mPa·s;

wherein the repeating texture is so designed to provide a network of channels that allows fluid communication of the coating composition when the first surface is worn on the skin.

Preferred embodiments of the pre-formed sheet compositions are described in Table 1 above. More preferably, the pre-formed sheets are made by the process described above.

The coating composition can be aqueous solutions, including gels, or emulsions such as oil-in-water emulsions, water-in-oil emulsions or multiple emulsions having aqueous or oily external phases. Preferred embodiments are described in Table 2 above, all of which have a viscosity of between about 5000 mPa·s and about 15,000 mPa·s. The viscosity of the coating composition is measured on a Brookfield viscometer using a heliopath T-bar C spindle at 5 rpm.

The weight ratio of the coating composition to the pre-formed sheet is generally more than about 1:50, preferably from about 1:25, more preferably from about 1:15 to about 10:1. Preferred dosage rates of the coating compositions on the pre-formed sheet can alternatively be expressed as from about 0.001 to about 0.2 g/cm$^2$, preferably from about 0.005 to about 0.05 g/cm$^2$. Generally, the coating composition covers at least about 20%, preferably at least about 50%, more preferably at least about 75% of the area of the first surface.

The cosmetic device herein can be made by any suitable process, preferably, by the process as described herein. In the embodiment above, the pre-formed sheet is placed into a blister package so that the first surface remains the lower surface in the package, the second surface to face the sealing of the package. Such packaging is advantageous for the cosmetic device herein. It is the intention that the wearer would remove the cosmetic device from the packaging with the fingers engaging the second surface, and then applying the first surface to the skin.

Figure 5:
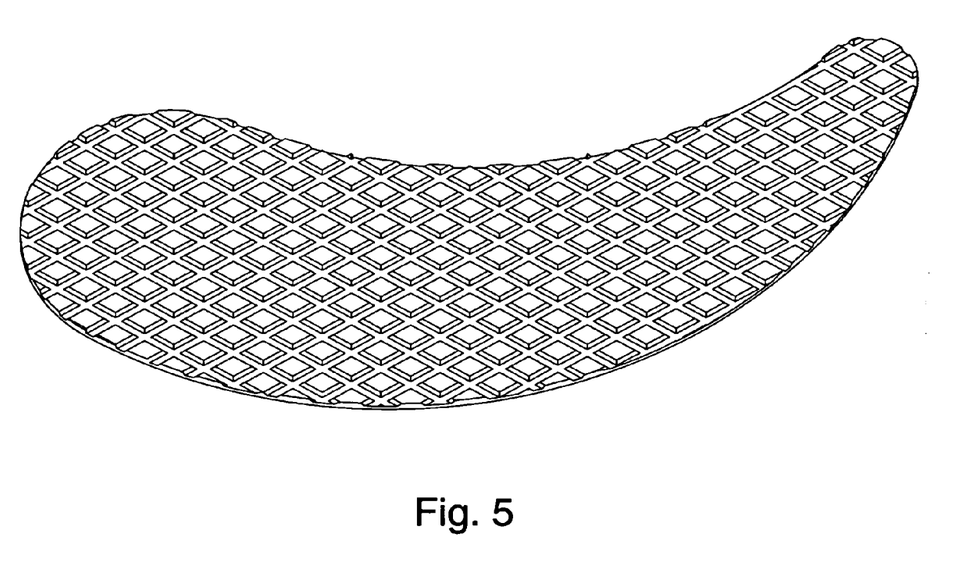
FIG. 5 is a perspective view of a preferred embodiment of the pre-formed sheet of the present invention.
Figure 6:
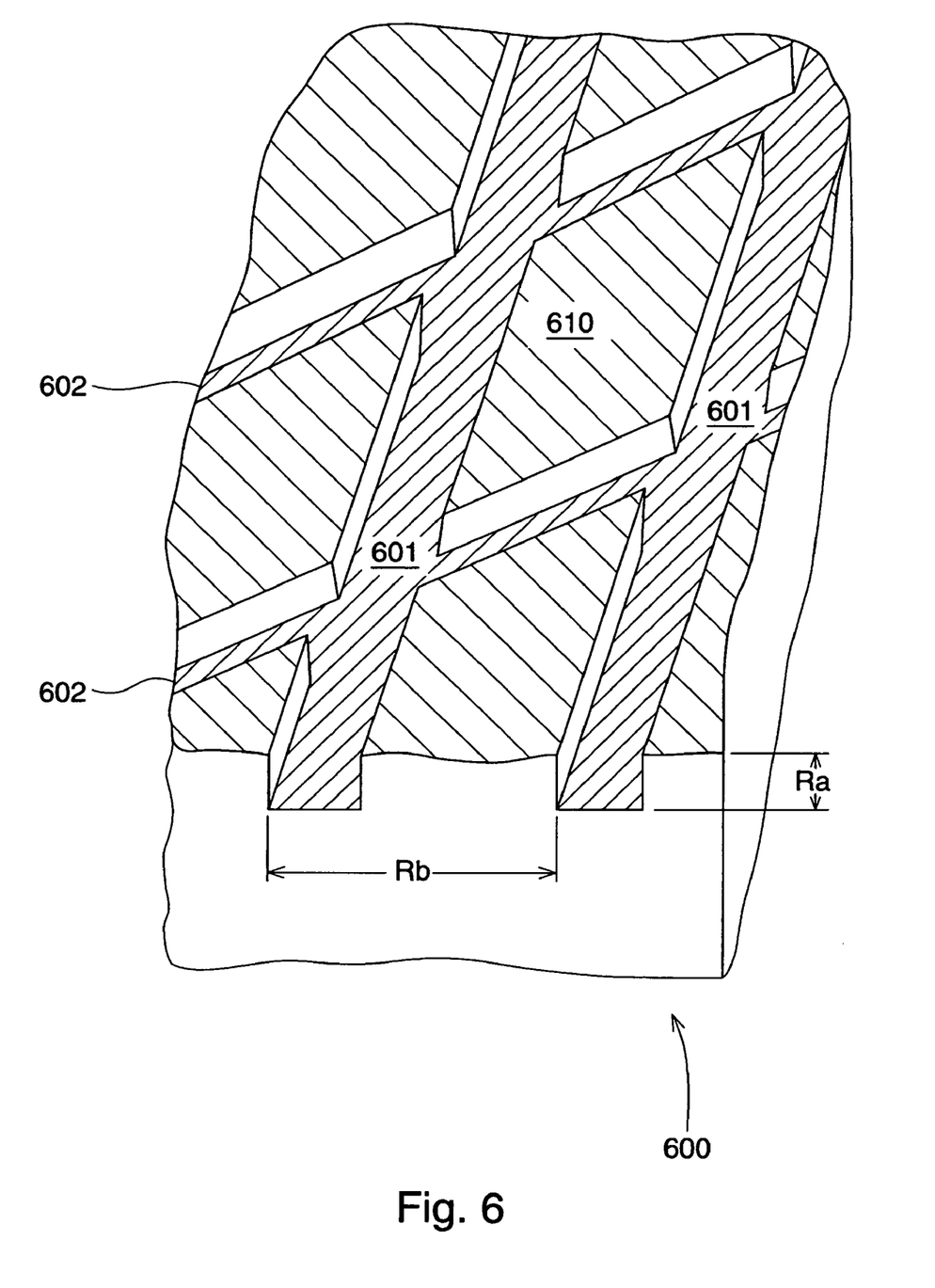
FIG. 6 is an enlarged, partially segmented perspective view of the first surface vicinity of a preferred embodiment of the pre-formed sheet of the present invention.

It has been surprisingly found that, by providing a certain thickness to the pre-formed sheet, and texture of certain depth and frequency to the first surface of the pre-formed sheet, the cosmetic device provides various benefits for the wearer of the cosmetic device. FIG. 6 is an enlarged, partially segmented perspective view of the first surface vicinity of a preferred embodiment of the pre-formed sheet of the present invention. Referring to FIG. 6, the first surface of the pre-formed sheet has a repeating texture that provides a network of channels (601). Despite the cosmetic device comprises a coating composition (not shown) of low viscosity, the pre-formed sheet can be conveniently adhered to the skin by applying the first surface to the skin. It has been surprisingly found that, with the elements above, the cosmetic device provides adequate adhesion to the skin such that, even when worn in a vertical manner, the cosmetic device does not easily drag down the skin. Without being bound by theory, it is believed that the network of channels that allow fluid communication of the coating composition provides an even distribution of the coating composition predominantly in the channels of the texture, thereby allowing the remaining wearer contacting area (610) of the texture to effectively adhere to the skin. Referring to FIG. 5, a highly preferred embodiment of the wearer contacting areas is depicted as the plurality of diamond shaped convexes. Referring back to FIG. 6, when the coating composition is excess the amount that can be carried in the channels, the network of channels also allows discretion of the coating composition to the peripheral (602) of the pre-formed sheet thereby allowing the coating composition to flow away from, or evaporate from the area of the skin on which the cosmetic device is applied. Thus, after the cosmetic device is worn on the skin, the coating composition immediately evenly distributes throughout the area on which the cosmetic device is worn, leaving the discontinuous, spaced wearer contacting areas more or less vacuum. Thus, the cosmetic device is sucked onto the skin. For such effective sucking of the cosmetic device on the skin, the pre-formed sheet is preferably uniform in thickness. The channels further provide a reservoir of the coating composition between the pre-formed sheet and the skin, thus allowing continuous contact of the coating composition to the skin so that the skin benefit agents are effectively delivered to the skin.

Providing rims around the peripheral of the pre-formed sheet has been proposed for increasing the strength of the pre-formed sheet. If the rim is overly distinct such that it interferes with the fluid communication of the channels, the rims may negatively affect the suction effect herein. Thus, when rims are provided to the pre-formed sheet, they are kept to a modest thickness and in a manner that provide continuity to the channels.

Preferably, the second surface of the pre-formed sheet also has a repeating texture having a depth of from about 10 μm to about 500 μm, preferably from about 50 μm to about 120 μm at a frequency of from about 0.2 to about 1 per mm, preferably from about 0.3 to about 0.7 per mm. Texturing on the second surface is also advantageous to the wearer. The first surface is intended to be applied to the skin. Upon removing the cosmetic device from the package, the wearer would engage the fingers on the second surface. The texturing of the second surface will help this engagement. Further, even if the wearer applies the second surface on the skin, the texturing of the second surface will provide similar effects as expected by the first surface. Further, from an aesthetic point of view, texturing on both surfaces provides a matte, less shiny appearance to the cosmetic device, thereby the cosmetic device is more or less invisible upon application to the skin.

METHODS OF USE

The cosmetic device of the present invention is applied to a target area of the skin, hair or nails, and will generally be left on the target area for at least 1 minute, preferably at least 5 minutes, it can be left on for a period of up to 12 hours, preferably up to 3 hours, more preferably up to 1 hour, though most preferably for less than 30 minutes. The cosmetic device can then be removed in one piece. Preferably, the first surface is worn on the skin.

In one embodiment, the cosmetic device may comprise the coating composition in excess amount, wherein the excess coating composition is first applied to the entire surface of the face, followed by applying the cosmetic device to a specific area of the face where intensive treatment is desired.

Depending on the skin benefit agent contained therein, the pre-formed, cosmetic devices of the present invention may have at least one of the following uses; hydrating the skin, hair or nails, smoothing fine lines and wrinkles; cosmetically treating acne; firming or softening the skin, strengthening; softening; exfoliating; improving and/or evening skin tone and/or texture; skin, hair or nail lightening; tanning; reducing the appearance of pores; absorbing or controlling secretions; protecting and/or soothing the skin, hair or nails, muscles, aches or pains; reducing puffiness, and/or dark circles; stimulating wound healing; warming, refreshing or cooling the skin, hair or nails; relieving inflammation; brightening the complexion; decongesting; reducing swelling; treating dermatological conditions; cushioning; purifying; fragrancing; reducing bacterial or micro-organism growth; healing; repelling insects; removing unwanted hair, dirt, or make-up; and coloring or bleaching the target area to which the cosmetic device is applied. Preferably, the pre-formed sheets herein are cosmetically used for hydrating the skin, hair or nails; smoothing fine lines and wrinkles; improving and/or evening the skin tone and/or texture; and firming or softening of the skin.

It is understood that the foregoing detailed description of examples and embodiments of the present invention are given merely by way of illustration, and that numerous modifications and variations may become apparent to those skilled in the art without departing from the spirit and scope of the invention; and such apparent modifications and variations are to be included in the scope of the appended claims.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for providing a packaged device, said device comprising a pre-formed sheet and a coating composition, said process comprising the steps of:
  a) providing an unsealed package;
  b) applying a coating composition in the package;
  c) placing a pre-formed sheet in the package, wherein said pre-formed sheet is made by a process comprising the steps of:
    i) providing a sol phase composition comprising from about 10% to about 99.5% water and from about 0.5% to about 20% polysaccharide gelling agent having a sol-gel transition point between about 25° C. and about 80° C.;
    ii) heating said sol phase composition to a temperature of at least 5° C. higher than the sol-gel transition point;
    iii) pre-cooling the sol phase composition to a temperature of between 0° C. and 5° C. higher than the sol-gel transition point;
    iv) forming first and second surfaces by pressing the pre-cooled sol phase composition between two liners, the two liners being supplied by two counter-rotating rollers facing each other, wherein the rollers further comprise cooling means and the two liners further provide textures to the first and second surfaces;
    v) cooling the pressed sol phase composition into a gel phase composition;
    vi) cutting the gel phase composition by a die to provide said pre-formed sheet;
  d) sealing the package;
wherein said pre-formed sheet is free of a supporting substrate and has a flex angle of from about 15° to about 80°, and wherein the steps a), b), c) and d) are in communication with each other to provide a continuous line process.

2. A process according to claim 1, wherein said coating composition is a cosmetic product.

3. A process according to claim 2, wherein said coating composition comprises a skin benefit agent.

4. A process according to claim 1, wherein said coating composition is a pharmaceutical product.

5. A process according to claim 1, wherein said coating composition is a food product.

* * * * *